US 11,439,751 B2

(12) United States Patent
Mansour

(10) Patent No.: US 11,439,751 B2
(45) Date of Patent: Sep. 13, 2022

(54) PASSIVE START DRIP CHAMBER

(71) Applicant: CareFusion 303, Inc., San Diego, CA (US)

(72) Inventor: George Mansour, Diamond Bar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 90 days.

(21) Appl. No.: 16/877,312

(22) Filed: May 18, 2020

(65) Prior Publication Data

US 2020/0397986 A1 Dec. 24, 2020

Related U.S. Application Data

(63) Continuation of application No. 15/672,917, filed on Aug. 9, 2017, now Pat. No. 10,653,832, which is a
(Continued)

(51) Int. Cl.
*A61M 5/40* (2006.01)
*A61M 5/168* (2006.01)
(Continued)

(52) U.S. Cl.
CPC ...... *A61M 5/16804* (2013.01); *A61M 5/1411* (2013.01); *A61M 5/162* (2013.01); *A61M 5/40* (2013.01); *A61M 39/227* (2013.01)

(58) Field of Classification Search
CPC ... A61M 5/1411; A61M 5/16804; A61M 5/40
See application file for complete search history.

(56) References Cited

U.S. PATENT DOCUMENTS

| 2,784,733 A | 3/1957 | Martinez |
| 4,005,710 A | 2/1977 | Zeddies et al. |
| (Continued) | | |

FOREIGN PATENT DOCUMENTS

| CN | 2201947 Y | 6/1995 |
| CN | 2721106 Y | 8/2005 |
| (Continued) | | |

OTHER PUBLICATIONS

Canadian Office Action for Application No. 2953111, dated Jul. 7, 2021, 3 pages.
(Continued)

*Primary Examiner* — Deanna K Hall
(74) *Attorney, Agent, or Firm* — Morgan, Lewis & Bockius LLP

(57) ABSTRACT

A drip chamber is described that is used in medical infusion therapy, wherein the drip chamber utilizes valving to control flow of one or more fluids to a patient. The drip chamber includes a body forming a chamber, wherein fluid may enter via two or more flow ports, and an output port, where fluid may exit the chamber. A float controls fluid flow through one or more flow ports into the chamber such that the flow exiting the chamber may be limited to a single fluid or a combination of the fluids entering the chamber. The float is configured to be retained within the chamber, and the float moves within the chamber based on a level of fluid within the chamber. The control characteristics of the float are determinable by attributing specific buoyancy and dimensions to the float.

18 Claims, 6 Drawing Sheets

Related U.S. Application Data continuation of application No. 14/319,576, filed on Jun. 30, 2014, now Pat. No. 9,731,070.

(51) Int. Cl.
*A61M 5/14* (2006.01)
*A61M 5/162* (2006.01)
*A61M 39/22* (2006.01)

(56) References Cited

U.S. PATENT DOCUMENTS

| | | | |
|---|---|---|---|
| 4,186,740 A * | 2/1980 | Guerra | A61M 5/36 137/188 |
| 4,256,103 A | 3/1981 | Mylrea | |
| 4,449,976 A | 5/1984 | Kamen | |
| 5,839,466 A | 11/1998 | Dutter | |
| 6,213,986 B1 | 4/2001 | Darling, Jr. | |
| 6,485,454 B1 | 11/2002 | Yueh | |
| 2006/0189945 A1 | 8/2006 | Adams | |
| 2007/0215637 A1 | 9/2007 | Kim | |
| 2009/0287152 A1 * | 11/2009 | Goodall | A61M 5/1411 604/127 |
| 2010/0024114 A1 | 2/2010 | Hand | |
| 2011/0208128 A1 | 8/2011 | Wu et al. | |
| 2011/0275988 A1 | 11/2011 | Davis et al. | |
| 2013/0331811 A1 | 12/2013 | Butterfield | |

FOREIGN PATENT DOCUMENTS

| | | |
|---|---|---|
| CN | 101574549 A | 11/2009 |
| CN | 102727957 | 10/2012 |
| CN | 102743809 | 10/2012 |
| CN | 102973997 | 3/2013 |
| CN | 101287513 B | 4/2013 |
| CN | 106470715 B | 3/2020 |
| JP | H07148256 | 10/1979 |
| JP | S54142995 U | 10/1979 |
| JP | S5335511 | 6/1995 |
| JP | 2007535981 A | 12/2007 |
| WO | WO-1997011729 A1 | 4/1997 |

OTHER PUBLICATIONS

Chinese Office Action for Application No. 202010105631.5, dated Jun. 21, 2021, 8 pages including translation.
Japanese Office Action for Application No. 2020157133, dated Jul. 30, 2021, 4 pages including translation.
Australian Office Action for Application No. 2015284633, dated Feb. 8, 2019, 3 pages.
Australian Office Action for Application No. 2015284634, dated Feb. 8, 2019, 5 pages.
Chinese Office Action for Application No. 201580035501.6, dated Feb. 2, 2019, pages.
Chinese Office Action for Application No. 201580035512.4, dated Feb. 3, 2019, 15 pages.
European Office Action for Application No. 15735782.3, dated Feb. 11, 2019, 4 pages.
European Office Action for Application No. 15735782.3, dated Jan. 30, 2020, 4 pages.
International Search Report and Written Opinion for Application No. PCT/US2015/036288, dated Sep. 17, 2015, 10 pages.
International Search Report and Written Opinion for Application No. PCT/US2015/036289, dated Oct. 2, 2015, 10 pages.
Japanese Office Action for Application No. 2016-575751, dated Mar. 29, 2019, 9 pages.
Canadian Office Action for Application No. 2953111, dated Mar. 21, 2022, 5 pages.

* cited by examiner

PASSIVE START DRIP CHAMBER

CROSS-REFERENCES TO RELATED APPLICATIONS

This application is a continuation of U.S. patent application Ser. No. 15/672,917, filed on Aug. 9, 2017, entitled "PASSIVE START DRIP CHAMBER," which is a continuation of U.S. patent application Ser. No. 14/319,576, filed on Jun. 30, 2014, now U.S. Pat. No. 9,731,070, entitled "PASSIVE START DRIP CHAMBER," each of which is hereby incorporated by reference in its entirety for all purposes.

This description relates in general to the field of medical fluid connectors, and in particular to a flow control drip chamber connector for use in medical infusion therapy.

BACKGROUND

Medical infusion therapy involves the administration of medication through a needle or catheter. The medication may be administered using intravenous, intramuscular, or epidural techniques. Typically, infusion therapy includes a fluid source coupled through tubing to a patient's intravenous needle or a catheter. The fluid, which may comprise medication or any other fluid, is usually dripped from the fluid source, through a fluid pathway, and into the patient. Typically, a primary fluid source and one or more secondary fluid sources may be joined to the fluid pathway between the source and the patient.

The primary and secondary fluid sources are joined in the fluid pathway such that the secondary fluid may be delivered concurrently the primary fluid. Alternatively, flow of the primary fluid may be halted during delivery of the secondary fluid and restarted after flow of the secondary fluid has ceased.

SUMMARY

An aspect of the present disclosure provides a passive start drip chamber device comprising: a chamber fluidly coupled to first and second input flow ports and an output flow port; a float disposed within the chamber, the float configured to move between an occluding configuration, wherein the first input flow port is occluded, and an open configuration, wherein the first input flow port is not occluded, based on a level of fluid within the chamber.

According to certain implementations of the present disclosure, a passive start drip chamber device comprises: a body with an interior chamber, the body having a first input flow port, a second input flow port, and an output flow port, the first input flow port comprises an opening fluidly coupled with the interior chamber; a float within the interior chamber, the float comprising a portion configured to extend into the opening; wherein the float is configured to rise and fall in the chamber based on a fluid level within the chamber, such that the portion moves relative to the opening between a closed configuration, wherein fluid through the first input flow port is occluded by the portion, and an open configuration, wherein the portion is withdrawn from the opening such that fluid is conducted through the opening and into to the chamber.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such as "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Figure 1:
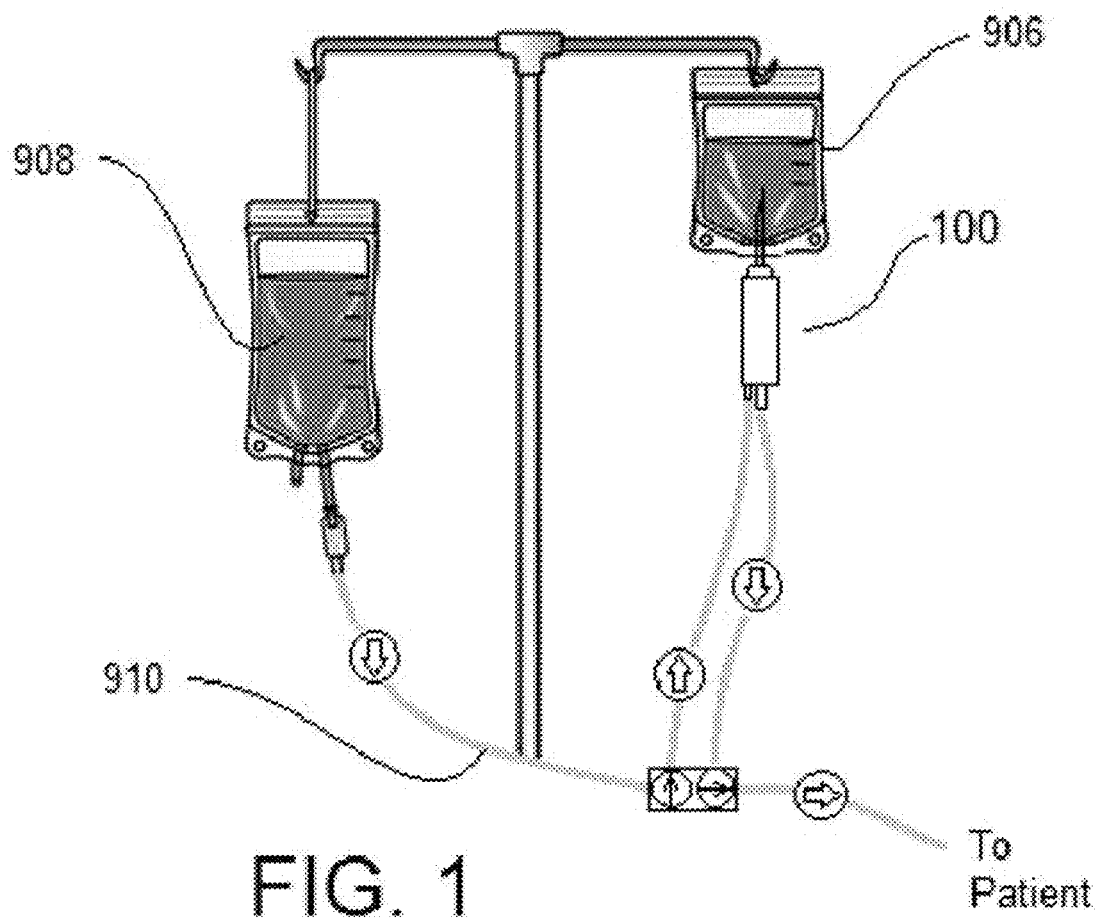
FIG. 1 illustrates a perspective view of embodiments of a passive start drip chamber in accordance with aspects of the present disclosure.
Figure 2:
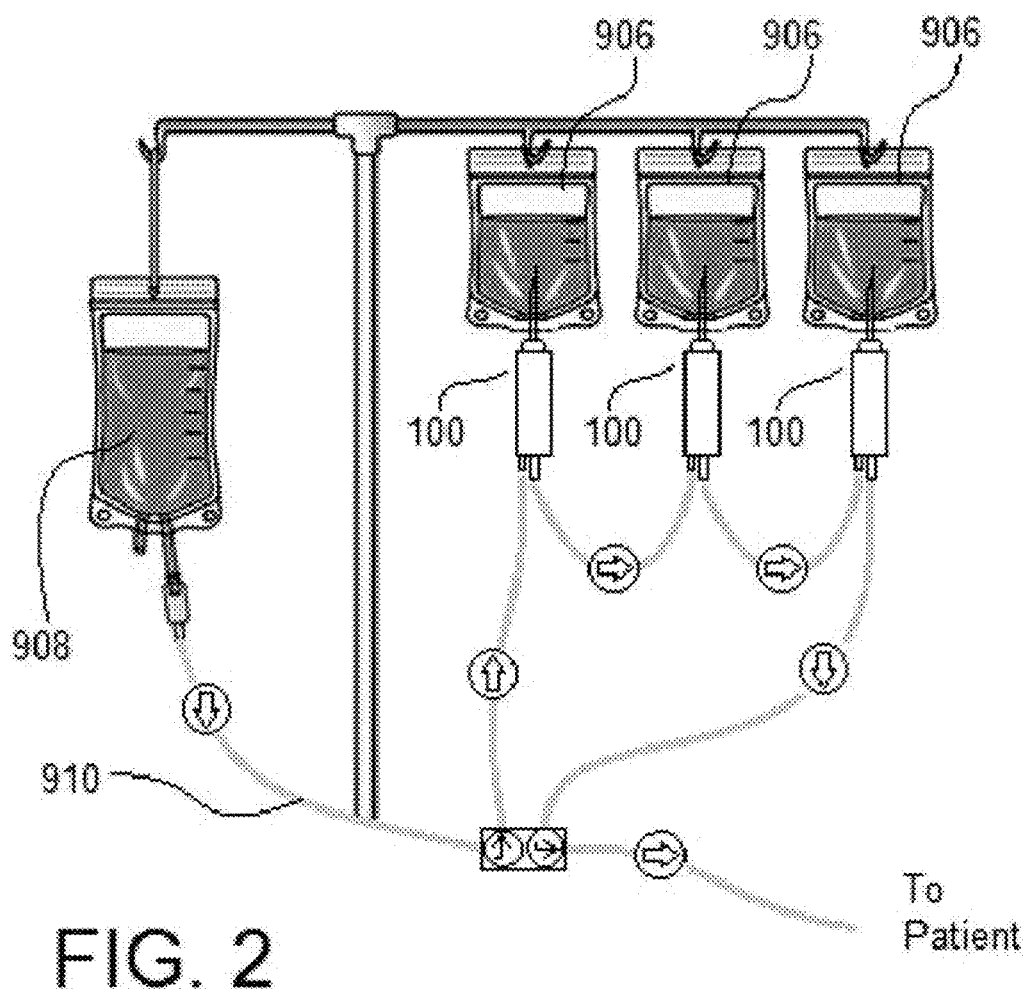
FIG. 2 illustrates a perspective view of embodiments of a passive start drip chamber in accordance with aspects of the present disclosure.
Figure 3A:
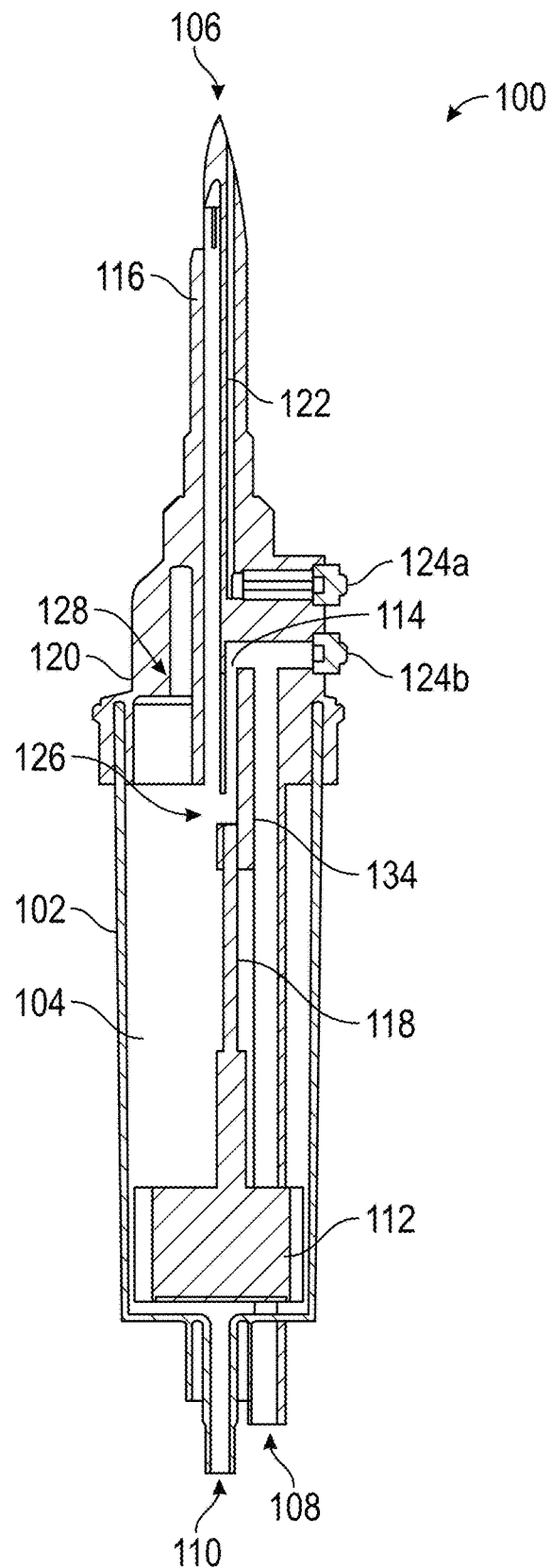
FIG. 3A illustrates a front section view of embodiments of a passive start drip chamber in an open configuration in accordance with aspects of the present disclosure.
Figure 3B:
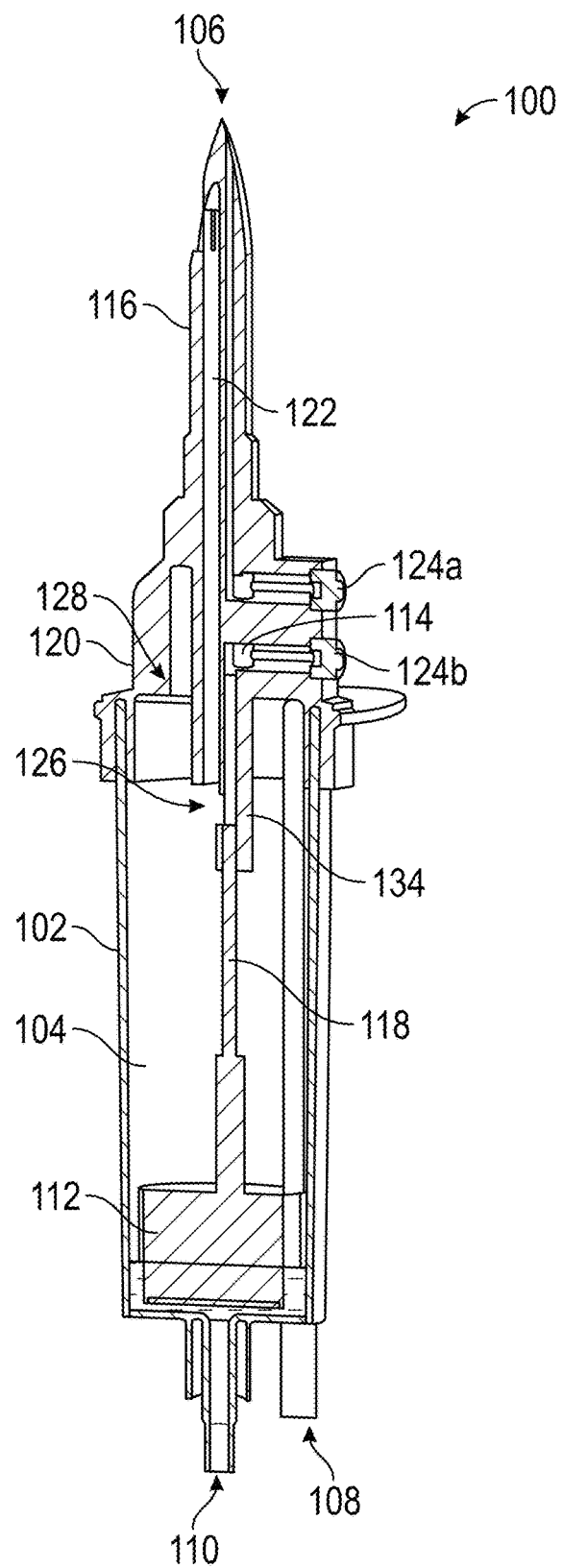
FIG. 3B illustrates a perspective section view of embodiments of a passive start drip chamber in an open configuration in accordance with aspects of the present disclosure.

The present disclosure relates to a passive start drip chamber for use in medical infusion therapy. FIG. 1 illustrates embodiments of a passive start drip chamber device 100 configured to control flow of a primary fluid source 908 and secondary fluid source 906 to a patient (not shown). The passive start drip chamber device 100 may be fluidly coupled to a secondary fluid source 906 and the fluid pathway 910 between a primary fluid source 908 and a patient. Upon coupling, flow from the primary fluid source 908 may be diverted to the passive start drip chamber device 100. The passive start drip chamber device 100 may then control flow of the primary fluid source 908 and the secondary fluid source 906 to the patient. Referring to FIG. 2, embodiments are illustrated having a plurality of passive start drip chamber devices 100 and secondary fluid sources 906 fluidly coupled to a fluid pathway 910 between a primary fluid source 908 and a patient (not shown).

Referring to FIGS. 3A-4B, the passive start drip chamber device 100 comprises a body 102 forming a chamber 104, two or more flow ports where fluid may enter the chamber 104 from a fluid source (e.g., an intravenous bag ("IV bag") or a line connected to an IV bag), and an output port 110 where fluid may exit the chamber 104. In some embodiments, the body 102 comprises a port where a primary fluid 908 may enter the drip chamber, a port where a secondary fluid 906 may enter the drip chamber, and a port for fluid to exit 110 the drip chamber. Each 906/908 port is fluidly connected to the chamber 104 within the body 102. In some embodiments, a secondary flow port 106 is disposed at a top of the body 102 (e.g., an end above or opposite the output port), while a primary flow port 108 and output flow port 110 are disposed along the body 102. The primary flow port 108 is fluidly coupled to a flow path 114 disposed through the body 102 such that fluid from the primary flow port 108 enters a top portion of the chamber 104. In some embodiments, the portion of the body 102 comprising the flow path 114 extends as a channel 134 from the top portion of the chamber 104, and in some embodiments, the portion of the body 102 comprising the flow path 114 extends as a channel 134 within an interior of the chamber 104 from the top portion of the chamber 104. The secondary flow port 106 is configured to couple with a secondary fluid source 906 such as a fluid bag. The secondary flow port 106 may be coupled with a fluid bag using a fluid fitting, including a luer-type fitting. In some embodiments, the secondary flow port 106 comprises an intravenous bag spike 116 having a lumen extending therein to fluidly couple the chamber with a fluid bag.

Figure 4A:
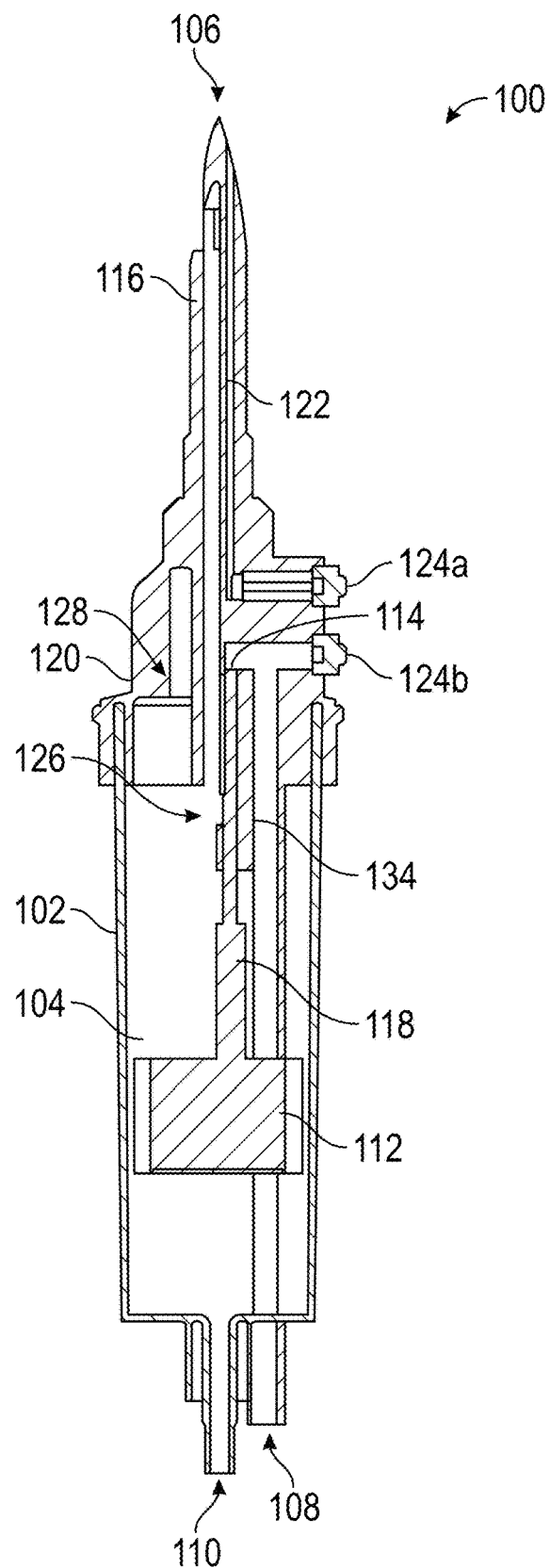
FIG. 4A illustrates a front section view of embodiments of a passive start drip chamber in an occluded configuration in accordance with aspects of the present disclosure.
Figure 4B:
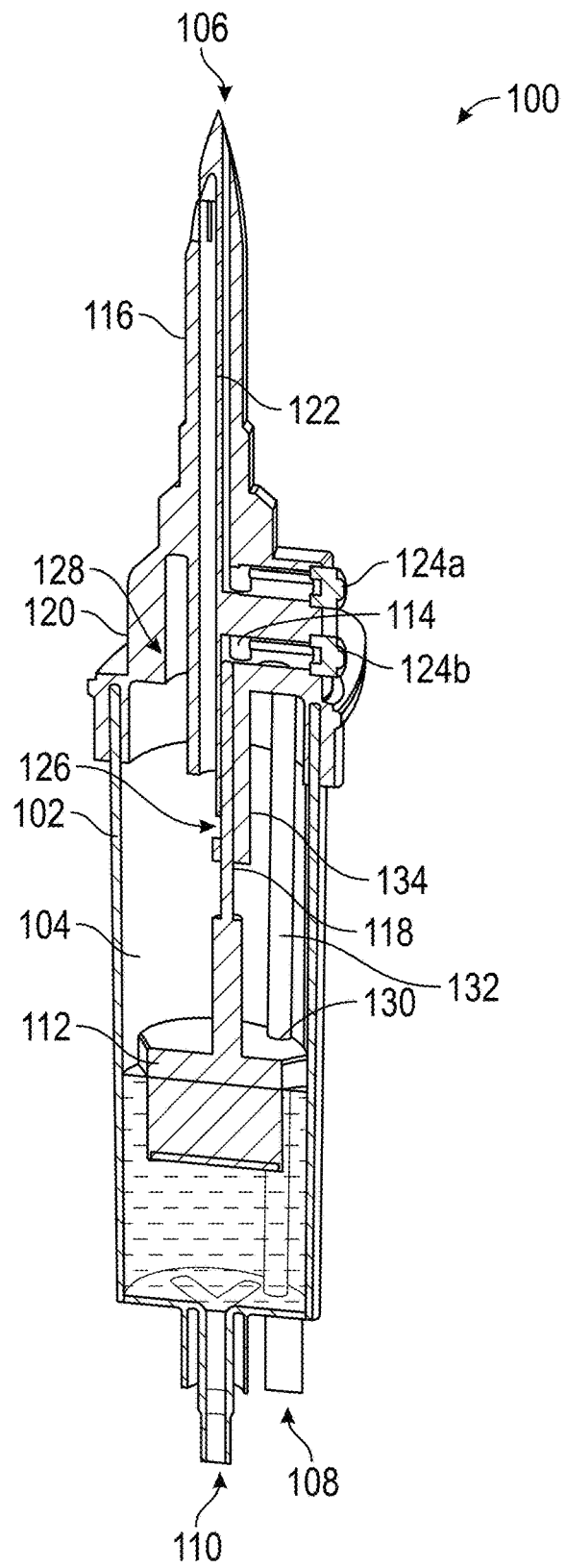
FIG. 4B illustrates a perspective section view of embodiments of a passive start drip chamber in an occluded configuration in accordance with aspects of the present disclosure.

Referring to FIG. 4B, flow from two or more fluid sources to a patient is controlled within the body 102. More specifically, flow of a primary fluid into the chamber 104 is reduced or halted as a secondary fluid enters the chamber 104. The flow of a primary fluid into the chamber 104 is stopped by the closing of a valve, fluid pathway, or fluid conduit within the chamber 104. Referring to FIG. 4B, as the flow of secondary fluid into the chamber 104 reduces or ceases, the fluid level within the chamber decreases, and the valve, fluid pathway, or fluid conduit opens and the primary fluid may once again flow into the chamber 104. By reducing or stopping flow of the primary fluid during flow of the secondary fluid, and then restarting flow of the primary fluid after flow of the secondary fluid has completed, complete and accurate delivery of the secondary fluid to the patient can be assured and provided with little or no subsequent adjustment by a caregiver.

The body 102 may be composed of a malleable yet resilient material that allows the walls of the body 102 to be flexible. For example, the walls may be sufficiently resilient to permit elastic deformation when the wall is collapsed to engage an opposing wall or structures within the chamber. In some embodiments, the walls of the body 102 may be squeezed to expel air or other gasses from within the chamber 104. Air may be expelled into the secondary fluid source, or through a valve 128, such as a hydrophobic filter, to the atmosphere. The body 102 and chamber 104 may be any size that achieves the desired flow rate and volume. For example, the chamber 104 volume may be selected to achieve a specific flow rate or to retain a specific valve size. The wall thickness of the body 102 may be selected to achieve a specific resiliency.

In some embodiments, the body 102 may have one or more flow ports in alternate or additional locations on the body 102. For example, the primary flow port 108 may be coupled to the body 102 parallel to the secondary flow port 106. In some embodiments, the secondary flow port 106 may be formed as a cap 120 coupled to the body 102 such that the cap 120 encloses the top portion of the chamber 104. In some embodiments, the cap 120 is removably coupled to the body, thereby providing access to the chamber 104. The cap 120 can include an auxiliary flow path 122. The auxiliary flow path 122 may be disposed through the cap, between the secondary flow port 106 and an access plug 124a on an external surface of the cap 120. The cap 120 may include an additional access plug 124b, providing access to the flow path 114 of the primary flow port 108.

In some embodiments, the valve includes a float 112 disposed within the chamber 104 between the secondary flow port 106 at the top of the chamber 104 and the output flow port 110 at the bottom of the chamber 104. The float 112 may be any shape but is preferably shaped to fit within the chamber 104 and may be configured to move axially between the top and bottom of the chamber 104.

Referring to FIG. 4B, the float 112 may be a cylinder having one or more axial grooves 130 on the outer surface, wherein the axial grooves are configured to mate with a rail, guide, or protrusion 132 along a surface of the chamber 104. The mating of the groove 130 and rail 132 allow the float to move axially within the chamber, yet prevent torsional rotation of the float. In some embodiments, the grooves 130 may be on an internal surface of the chamber, and the rail, guide, or protrusions 132 may be on the outer surface of the float 112.

The diameter of the float 112 may be selected to assure stability within the chamber during movement, yet allow fluid to flow around the float 112. In some embodiments, the grooves 130 or indentations provide a fluid flow path around the float 112. In some embodiments, the chamber 104 comprises an annular ring or seat such that the output port 110 becomes fluidly sealed when the float 112 is in a lowest position within the chamber, thereby preventing or reducing the likelihood of air from passing through the chamber 104 to the patient or to a pump.

The float 112 may comprise specific buoyancy, causing it to raise or lower with a specific fluid level. The float 112 may be solid or hollow, and may comprise air or foam. Preferably, the float 112 material will not degrade in the environment of the chamber 104. In some embodiments, the buoyancy of the float 112 is adjustable. For example, the float 112 may comprise a dial or selector to adjust buoyancy.

Referring to FIGS. 4A-4B, a portion of the float 112 may include a protrusion 118 that extends from the float 112 toward the top of the chamber. In some embodiments, the protrusion can extend in other directions, depending on the relative orientation of the float with respect to flow channels of the device. At least a portion of the protrusion 118 extends into the flow path 114 of the primary flow port 108 at the top of the drip chamber 104. When the float 112 is at a lowest position adjacent to the output flow port 110, for example, when no flow from the secondary flow port 106 is present, the protrusion 118 partially extends into the flow path 114. In some embodiments, a portion of the cap 120 extends into the chamber 104, down from a top portion of the chamber, and comprises the flow path 114. The portion of the cap 120 that extends into the chamber 104 may further comprise a channel 134 that provides fluid communication between the flow path 114 and the chamber 104. The channel 134 may be disposed along the flow path 114 and through the portion of the cap 120 that extends into the chamber 104.

When the protrusion 118 is only partially extended into the channel 134, the aperture 126 allows fluid to flow through the primary flow port 108, through the flow path 114 and channel 134, and through the aperture 126 into the chamber 104. As flow from the secondary flow port 106 enters the chamber 104, the float 112 rises in the drip chamber 104. As the float 112 rises within the chamber 104, the protrusion 118 advances along the channel 134 thereby blocking flow through the aperture 126, occluding the flow path 114, and halting flow from the primary flow port 108 into the chamber 104. Upon a reduction or cessation of flow from the secondary flow port 106 into the chamber 104 the float 112 lowers, thereby retracting or withdrawing the protrusion 118 along the channel 134, exposing the aperture 126, and allowing flow from the primary flow port 108 to enter the chamber 104 and ultimately exit from the output port 110.

In some embodiments, the float 112 includes two or more protrusions 118, whereby two or more flow ports into the chamber 104 may be controlled. For example, the float 112 may include two protrusions 118 having varying lengths. When the float 112 rises, the longer protrusion 118 would occlude a first fluid flow port before the shorter protrusion occludes a second fluid flow port. In this example, flow from the second fluid flow port into the chamber 104 would continue until the float 112 rises to a level that causes the shorter protrusion 118 to also occlude the second fluid flow port.

In some embodiments, the body 102 comprises two or more chambers 104 and floats 112, allowing for two or more primary or secondary fluids to be coupled with the passive start drip chamber device 100. In some embodiments, a lower float 112 and upper float 112 are linearly disposed within the chamber 104, allowing for control of several fluid flows into the chamber 104. For example, the lower float 112 may have a protrusion 118 that extends through and aperture in the upper float 112. Alternatively, the upper float 112 may have a surface indentation configured to allow the protrusion 118 of the lower float 112 to move along side of the upper float 112. In some embodiments, a first float 112 and second float 112 are disposed in parallel within the chamber 104. For example, each float 112 may comprise a protrusion 118 to control a flow port leading into the chamber 104.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

Described herein are at least the following concepts:

Concept 1. A passive start drip chamber device comprising:
a chamber fluidly coupled to first and second input flow ports and an output flow port;
a float disposed within the chamber, the float configured to move between an occluding configuration, wherein the first input flow port is occluded, and an open configuration, wherein the first input flow port is not occluded, based on a level of fluid within the chamber.

Concept 2. The device of concept 1, wherein the float comprises an elongate member that occludes the first input flow port when the float is in the occluding configuration.

Concept 3. The device of concept 2, wherein the elongate member resides within a flow path channel of the first input flow port, and axial movement of the float within the chamber translates to axial movement of the elongate member along the flow path channel.

Concept 4. The device of concept 1, wherein the float is configured to move from the occluding configuration toward the open configuration when fluid flow through the second input flow port reduces such that the level of fluid within the chamber drops below a filled threshold.

Concept 5. The device of concept 1, wherein the float is configured to move from the open configuration toward the occluding configuration when the level of fluid within the chamber exceeds a drained threshold.

Concept 6. The device of concept 1, wherein the first input flow port comprises a channel configured to conduct fluid to the chamber, and the float comprises an occluding portion disposed within the channel that moves along the channel and occludes or opens the port when the float is in the respective occluding or open configurations.

Concept 7. The device of concept 1, wherein at least a portion of a wall of the chamber is sufficiently resilient to permit elastic deformation when the wall is collapsed to engage an opposing wall or structures within the chamber.

Concept 8. The device of concept 1, wherein the second input port comprises a fluid connector configured to fluidly couple with a fluid source.

Concept 9. The device of concept 8, wherein the fluid connector comprises an intravenous bag spike having a lumen extending therein to conduct fluid.

Concept 10. The device of concept 1, further comprising a valve fluidly coupled to the chamber, the valve configured to release a gas from within the chamber.

Concept 11. The device of concept 1, wherein a top of the chamber, opposite the output flow port, comprises a removable cap.

Concept 12. The chamber of concept 11, wherein the removable cap comprises at least one of the first or second input flow ports.

Concept 13. The device of concept 1, wherein each of the float and the chamber comprise either an axial groove or a corresponding protrusion, the groove and protrusion configured to matingly align the float within the chamber.

Concept 14. The device of concept 1, wherein the float is configured to occlude the output flow port when the level of fluid within the chamber drops below a drained threshold.

Concept 15. A passive start drip chamber device comprising:
  a body with an interior chamber, the body having a first input flow port, a second input flow port, and an output flow port, the first input flow port comprises an opening fluidly coupled with the interior chamber;
  a float within the interior chamber, the float comprising a portion configured to extend into the opening;
  wherein the float is configured to rise and fall in the chamber based on a fluid level within the chamber, such that the portion moves relative to the opening between a closed configuration, wherein fluid through the first input flow port is occluded by the portion, and an open configuration, wherein the portion is withdrawn from the opening such that fluid is conducted through the opening and into to the chamber.

Concept 16. The device of concept 15, further comprising a channel fluidly coupled to the opening, wherein the float portion is configured to extend along and move within the channel.

Concept 17. The device of concept 15, wherein at least a portion of the chamber wall is sufficiently resilient to permit elastic deformation when the wall is collapsed to engage an opposing wall or structures within the chamber.

Concept 18. The device of concept 15, further comprising a valve coupled to the chamber, the valve configured to release a gas from within the chamber.

Concept 19. The device of concept 15, wherein a top portion of the chamber, opposite the output flow port, comprises a removable cap.

Concept 20. The device of concept 19, wherein the removable cap comprises at least one of the first or second input flow ports.

What is claimed is:

1. A passive start drip chamber device comprising:
    a body having a top portion and a bottom portion, a chamber formed between the top and bottom portions of the body, a first input flow port at the bottom portion of the body, a second input flow port at the top portion of the body, and an output flow port;
    a first input flow path coupled to and extending from the first input flow port to the top portion of the body such that a fluid flow through the first input flow path enters the chamber through the top portion of the body; and
    a float positioned within the chamber, between the top portion of the body and the bottom portion of the body, the float configured to move between an occluding configuration, wherein the first input flow path is occluded, and an open configuration, wherein the first input flow path is not occluded, based on a level of fluid within the chamber.

2. The passive start drip chamber device of claim 1, wherein the top portion of the body comprises a channel that extends into the chamber, wherein the first input flow path extends through the channel.

3. The passive start drip chamber device of claim 1, wherein the float comprises an elongate member that extends from the float toward the top portion of the body, the elongate member configured to occlude a channel of the body when the float is in the occluding configuration.

4. The passive start drip chamber device of claim 1, wherein the float is configured to move toward the occluding configuration when a first volume of fluid is within the chamber, and the float is configured to move toward the open configuration when a second volume of fluid, less than the first volume, is within the chamber.

5. The passive start drip chamber device of claim 1, wherein the float comprises a groove that extends along an outer surface of the float, the groove configured to permit a fluid to move through the chamber, between the top and bottom portions of the body.

6. The passive start drip chamber device of claim 1, wherein any of the float and the chamber comprise an elongate groove or elongate protrusion, and the other of the float and the chamber comprise the other of an elongate groove or an elongate protrusion, wherein the elongate protrusion and the elongate groove are configured to matingly align the float within the chamber.

7. The passive start drip chamber device of claim 1, wherein top portion of the body comprises an intravenous bag spike having a lumen fluidly coupled with the second input flow port.

8. The passive start drip chamber device of claim 1, further comprising a valve coupled to the chamber, the valve configured to release a gas from within the chamber.

9. The passive start drip chamber device of claim 1, wherein a wall of the body, between the top and bottom portions of the body, is sufficiently resilient to permit elastic deformation when collapsed to engage an opposing wall or structures within the chamber.

10. A passive start drip chamber device comprising:
a body having a top portion and a bottom portion, a chamber formed between the top and bottom portions of the body, a first input flow port at the bottom portion of the body, a second input flow port at the top portion of the body, and an output flow port, wherein a first input flow path is coupled to and extends from the first input flow port to a channel at a top portion of the body; and
a float positioned within the chamber, between the channel and the output flow port, the float configured to move toward and away from the channel based on a fluid level within the chamber, such that in an occluding configuration, the channel is occluded by the float, and in an open configuration, the channel is not occluded.

11. The passive start drip chamber device of claim 10, wherein the first input flow path extends through the channel.

12. The passive start drip chamber device of claim 10, wherein the float comprises an elongate member that extends from the float toward the top portion of the body, the elongate member configured to occlude the channel of the body when the float is in the occluding configuration.

13. The passive start drip chamber device of claim 10, wherein the float is configured to move toward the occluding configuration when a first volume of fluid is within the chamber, and the float is configured to move toward the open configuration when a second volume of fluid, less than the first volume, is within the chamber.

14. The passive start drip chamber device of claim 10, wherein the float comprises a groove that extends along an outer surface of the float, the groove configured to permit a fluid to move through the chamber, between the top and bottom portions of the body.

15. The passive start drip chamber device of claim 10, wherein any of the float and the chamber comprise an elongate groove or an elongate protrusion, and the other of the float and the chamber comprise the other of an elongate groove or elongate protrusion, wherein the elongate protrusion and the elongate groove are configured to matingly align the float within the chamber.

16. The passive start drip chamber device of claim 10, wherein the top portion of the body comprises an intravenous bag spike having a lumen fluidly coupled with the second input flow port.

17. The passive start drip chamber device of claim 10, further comprising a valve coupled to the chamber, the valve configured to release a gas from within the chamber.

18. The passive start drip chamber device of claim 10, wherein a wall of the body, between the top and bottom portions of the body, is sufficiently resilient to permit elastic deformation when collapsed to engage an opposing wall or structures within the chamber.

* * * * *